United States Patent [19]

Trager et al.

[11] Patent Number: 4,539,330

[45] Date of Patent: Sep. 3, 1985

[54] IMIDAZOLIDINYL UREA AND DERIVATIVES THEREOF FOR USE IN OPTHALMIC SOLUTIONS

[75] Inventors: Seymour F. Trager, Plainview, N.Y.; Victoria S. Chylinski, Stroud, England

[73] Assignee: Ketchum & Co. Inc., Westport, Conn.

[21] Appl. No.: 664,926

[22] Filed: Oct. 24, 1984

Related U.S. Application Data

[63] Continuation of Ser. No. 477,847, Mar. 22, 1983, abandoned.

[51] Int. Cl.³ .............................................. A61K 31/415
[52] U.S. Cl. ..................................................... 514/398
[58] Field of Search .................................... 424/273 R

[56] References Cited

U.S. PATENT DOCUMENTS

| | | | |
|---|---|---|---|
| 4,166,860 | 9/1979 | Douglas et al. | 424/273 R |
| 4,265,902 | 5/1981 | Van Ewijk | 424/273 R |
| 4,271,176 | 6/1981 | Berke et al. | 424/273 R |

OTHER PUBLICATIONS

Chem. Abst., 77, 105512(m) (1972)—Fontana et al.
Chem. Abst., 77, 105513(n) (1972)—Proserpio.
Chem. Abst., 86, 127,093(p) (1977)—Rosen et al.

*Primary Examiner*—Douglas W. Robinson
*Attorney, Agent, or Firm*—McAulay, Fields, Fisher, Goldstein & Nissen

[57] ABSTRACT

Anti-bacterial properties are imparted to a broad spectrum of ophthalmically active compositions by the inclusion therein of a urea derivative.

5 Claims, No Drawings

IMIDAZOLIDINYL UREA AND DERIVATIVES THEREOF FOR USE IN OPTHALMIC SOLUTIONS

This is a continuation of application Ser. No. 477,847, filed Mar. 22, 1983 now abandoned.

This invention relates to a composition and method for treating contact lenses and preserving ocular medications. More particularly, this invention relates to a composition and method for soaking and sterilizing contact lenses and preserving ocular medications in a sterile state.

BACKGROUND OF THE PRIOR ART

Both hard and so-called soft contact lenses have been described in the prior art. For example, U.S. Pat. No. 3,503,393 to Siederman, as well as U.S. Pat. No. 2,976,576 to Wichterle, describe processes for producing hydrophilic polymers of poly and (hydroxy-ethyl methacrylate) in aqueous reaction media having a sparingly cross-linked polymeric hydro-gel structure and having the appearance of elastic, soft, transparent hydrogels. Other soft contact lenses include those produced from silicones and other optically suitable materials.

The primary virtues of these lenses are their softness and optical suitability. These hydrophilic lenses are particularly desirable in opthalmology due to their quite remarkable ability to absorb water with a concomitant swelling to a soft mass of extremely good mechanical strength, complete transparency and an ability to retain shape and dimensions when subjected to equilibration in a given fluid.

One of the problems associated with such soft contact lenses, as well as hard contact lenses, is the method of their sterilization and cleaning. The very property of the hydrophilic soft lenses which allows them to absorb up to about 150 percent by weight of water also allows preservatives, which might otherwise be used for cleaning and sterilization to be absorbed, even concentrated and later released when the lens is positioned in the eye of the user. The release may be much slower than the uptake, thereby causing a buildup of the preservative material in the lenses. Such buildup eventually adversely affects the physical characteristics of the lenses including dimension, color, and the like. This can exhibit the harmful result of damaging or staining the contact lens itself and/or harming the delicate tissues of the conjunctivae and/or cornea of the user.

Hard contact lenses do not absorb appreciable amounts of water, only on the order of from about 0.1 to 0.4 percent by weight; consequently, the employment of effective preservatives does not create problems of the magnitude attendant soft contact lenses. Users of soft contact lenses are cautioned that solutions designed for use with hard contact lenses should be avoided, for the reason that the preservatives present in such solutions will be absorbed, even concentrated by the soft lens material, and may seriously damage the lens and/or tissue of the eyes of the user.

U.S. Pat. No. 3,689,693 discloses a process of soaking and sterilizing hydrophilic soft contact lenses. Therein, it is disclosed that a number of anti-microbial agents may be absorbed and concentrated in soft lenses, also suggesting that these materials may cause corneal damage and that similar in vitro and in vivo testings have demonstrated the undesirability of such anti-microbial agents when used with hydrophilic lenses.

OBJECTIVES OF THE INVENTION

An object of the present invention is to provide an anti-microbial agent for ophthalmic solutions designed for and adapted to general use in the eyes of humans and domestic animals.

A further object of the present invention is to provide an anti-microbial agent for use in solutions employed as cleaning, lubricating and/or cushioning agents for both hard and soft contact lenses.

A still further object of the invention is to provide an anti-microbial agent for use in artificial tear formulations.

SUMMARY OF THE INVENTION

It has been discovered that superior anti-microbial properties are imparted to solutions designed for use in and contact with the human eye by the inclusion of imidazolidinyl urea and imidazolidinyl urea derivatives.

Particularly preferred for use in formulating the effective compositions of the present invention are imidazolidinyl urea and N-(hydroxymethyl)-N-(1, 3-dihydroxymethyl-2, 5-dioxy-4-imidazolidinyl)-N'-(hydroxymethyl) urea.

The urea derivative may be employed in the selected ophthalmic solutions in a broad range of concentration, from about 0.01 to about 3 percent by weight.

The stabilized solutions thus provided exhibit an extreme level of compatibility with ocular tissues and are highly stable through a wide range of temperatures, including those attained in autoclaving, e.g., on the order of about 250° F.

One characteristic peculiar to the soft contact lens is the requirement that treating solutions used therewith contain no component which can be entrained in the latice of the gel, since such materials tend to accumulate and become irritating to the ocular tissue.

It has been observed, in clinical studies, that entrainment does not occur to any significant degree in the use of the imidazolidinyl urea and derivatives thereof iw soft contact lens cleaning solutions.

The following example serves to illustrate the efficacy of the basic solutions of the present invention.

EXAMPLES 1-3

| Ingredients | mg/ml |
| --- | --- |
| Sodium chloride USP | 7.0 |
| Boric acid USP | 4.42 |
| Sodium borate USP | 0.875 |
| Imidazolidinyl urea | 1.0 (0.1%) |
| | 2.0 (0.2%) |
| | 3.0 (0.3%) |
| EDTA USP | 1.0 |
| Water | to 1 ml |

The pH was adjusted to 7.2 and the solutions packaged in sterile containers.

The solution containing 0.3 percent urea derivative was used to perform a twenty-one day ocular irritation study in adult albino rabbits. Contact lenses were soaked overnight in the preservative solution with the solution changed every two days.

The lenses employed in the testing were 12.5/750 deltafilcon A with 43% water content. Each morning, the lenses were placed in the right eyes of six test animals and allowed to remain in position for a period of twelve hours. The eyes were evaluated immediately after lens placement, five minutes thereafter and at six and twelve hours thereafter.

At weekly intervals, a complete slitlamp evaluation was performed which included evaluation of corneal clarity, anterior chamber reaction, iris appearance and the presence or absence of conjunctival infection. The upper and lower lids were everted and the presence or absence of follicles and/or papillae noted.

Five of the six rabbits exhibited mild injection immediately after placement of the lens, which disappeared after five minutes. All eyes were white and quiet during the test period. Except for the transient injection, slit lamp examination of all anterior ocular structures was totally normal and no follicles, papillae or discharge were present at any time. All animals remained healthy during the test period with no gross change in weight.

Gross examination of the eyes as completely within normal limits, including the conjunctiva, cornea, iris, lens, ciliary body, vitreous, lens and optic nerve.

The anti-microbial agents are fully effective as evidenced by their satisfaction of the anti-microbial tests outlined in U.S. Pharmacopeia.

The anti-microbial activity of the urea derivatives also renders the inclusion of the agent in ophthalmic treating solutions such as medicament delivery systems of value. Examples of medicaments with which the anti-microbial agents of the present invention may be used are pilocarpine hydrochloride, hydro-cortisone, neomycin sulfate, bacitracin or the like. The foregoing list is intended to be merely exemplary and the urea derivatives serve to function across a wide spectrum of biologicals.

What is claimed is:

1. A process for imparting anti-microbial properties to an ophthalmic solution containing an opthalmically active ingredient comprising adding to said ophthalmic solution material an anti-bacterially effective amount of a urea derivative selected from the group consisting of imidazolidinyl urea and N-(hydroxymethyl)-N-(1, 3-dihydroxymethyl-2, 5-dioxy-4-imidazolidinyl)-N'-(hydroxymethyl)urea.

2. The process of claim 1 wherein said urea derivative is present in said solution in an amount of from 0.01 to 0.3% by weight.

3. The process of claim 1 wherein said ophthalmically active ingredient is an artificial tear aid.

4. The process of claim 1 wherein said ophthalmically active ingredient is a contact cleansing material.

5. The process of claim 1 wherein said ophthalmically active ingredient is an ophthalmically active medicament.

* * * * *